United States Patent [19]

Pallie et al.

[11] Patent Number: 4,617,357

[45] Date of Patent: Oct. 14, 1986

[54] PROCESS FOR REDUCING THE CONTENT OF CHLORINE IN GLYCIDYL COMPOUNDS

[75] Inventors: Kemal D. Pallie, Choëx; Gerald Dessauges, Montreux, both of Switzerland

[73] Assignee: Ciba-Geigy Corporation, Ardsley, N.Y.

[21] Appl. No.: 776,319

[22] Filed: Sep. 16, 1985

[30] Foreign Application Priority Data

Sep. 24, 1984 [CH]  Switzerland ........................ 4556/84

[51] Int. Cl.$^4$ ............................................. C08G 59/14
[52] U.S. Cl. ..................................... 525/506; 549/542; 525/523; 528/87; 528/373; 528/421; 528/485
[58] Field of Search .................. 525/506, 523; 528/87, 528/421, 373, 485; 549/542

[56] References Cited

U.S. PATENT DOCUMENTS 4,017,523  4/1977  Vargiu et al. .
4,485,221  11/1984  Krueger et al. ...................... 525/507
4,511,710  4/1985  Wang et al. ...................... 525/506 X
4,535,150  8/1985  Hunter ................................ 528/489

FOREIGN PATENT DOCUMENTS 58-173116  10/1983  Japan .
 1278737   6/1972  United Kingdom .

OTHER PUBLICATIONS

Lee & Neville, "Handbook of Epoxy Resins", 1967, pp. 4–30.
H. G. Kuivila, Synthesis, 10, 499 (1970).

Primary Examiner—Earl Nielsen
Attorney, Agent, or Firm—Luther A. R. Hall

[57] ABSTRACT

To reduce the content of chlorine in glycidyl compounds, in which the glycidyl groups are bonded to ether-oxygen, N or S atoms, these compounds are dissolved in a halogen-free inert organic solvent and reacted with a tin hydride of the formula I or II $$R_3SnH \qquad (I)$$

or $$R_2SnH_2 \qquad (II)$$

in which each radical R independently of one another is alkyl with 1 to 4 C atoms or phenyl, at least 1 equivalent of the tin hydride of the formula I or II being employed per equivalent of chlorine present, in the presence of a catalytic amount of an initiator which forms free radicals. The glycidyl compounds are then isolated from the reaction solution.

11 Claims, No Drawings

PROCESS FOR REDUCING THE CONTENT OF CHLORINE IN GLYCIDYL COMPOUNDS

The present invention relates to a process for reducing the content of chlorine in glycidyl compounds by reaction with organic tin hydrides in the presence of initiators which form free radicals.

It is known that the glycidyl compounds prepared by means of epichlorohydrin, especially those prepared industrially, are always contaminated with chlorine, which is present in the epoxy resin as ionic chlorine and in the glycidyl compound as hydrolysable chlorine (1,2-chlorohydrin) and as non-hydrolysable chlorine (methyl chloride).

Continually higher requirements in respect of purity are being imposed on epoxy resins, in particular those which are used for the production of electrical and electronic components, in order to reduce the corrosion influence of the residual chlorine content on substrates, in particular contact metals.

Many methods have already been disclosed for removing the residual chlorine content from epoxy resins. As documented in "Handbook of Epoxy Resins" (1967), 4–30, by H. Lee and K. Neville, these methods also have disadvantages.

Specific processes for the preparation of polyglycidyl ethers by two dehydrohalogenation reactions by means of sodium hydroxide solution are disclosed both in British Patent No. 1,278,737 and in German Offenlegungsschrift No. 2,523,696. The amount of total chlorine in the polyglycidyl ethers obtained according to the process is still relatively high. Japanese Preliminary Published Patent Application No. 58-173116 proposes removal of the residual chlorine content in epoxy resins by means of silver salts of organic acids. Apart from the fact that this is an expensive process, our own repeat work has shown that the effect achieved by this process is slight.

It is furthermore known, from "Synthesis", No. 10, October 1970, pages 499–509, that organo-tin hydrides are reducing agents with a selective action and are suitable, for example, for reducing halogenoalkanes, acid halides, aldehydes, ketones, esters and isocyanates.

It has now been found that the residual chlorine content in glycidyl compounds can be reduced with certain organo-tin hydrides without the glycidyl group thereby being attacked.

The present invention thus relates to a process for reducing the content of chlorine in glycidyl compounds in which the glycidyl groups are bonded to ether-oxygen, N or S atoms, which comprises reacting the glycidyl compound, dissolved in a halogen-free inert organic solvent, with a tin hydride of the formula I or II $$R_3SnH \qquad (I)$$

or $$R_2SnH_2 \qquad (II)$$

in which each radical R independently of one another is alkyl with 1 to 4 C atoms or phenyl, at least 1 equivalent of the tin hydride of the formula I or II being employed per equivalent of chlorine present, in the presence of a catalytic amount of an initiator which forms free radicals, and then isolating the glycidyl compound from the reaction solution.

Glycidyl compounds which are suitable for the process according to the invention and in which the glycidyl groups are bonded directly to ether-oxygen atoms are the polyglycidyl ethers, which are obtainable by reacting a compound containing at least two free alcoholic and/or phenolic hydroxyl groups per molecule with epichlorohydrin, glycerol dichlorohydrin or β-methylepichlorohydrin under alkaline conditions, or in the presence of an acid catalyst with subsequent treatment with an alkali. These ethers can be prepared with the glycidylating agents mentioned from, for example, acyclic alcohols, such as ethylene glycol, diethylene glycol and higher poly-(oxyethylene)-glycols, propane-1,2-diol and poly(oxypropylene)-glycols, propane-1,3-diol, poly-(oxytetramethylene)-glycols, pentane-1,5-diol, hexane-2,4,6-triol, glycerol, 1,1,1-trimethylolpropane, pentaerythritol and sorbitol, from cycloaliphatic alcohols, such as resorcitol, quinitol, bis-(4-hydroxycyclohexyl)-methane, 2,2-bis-(4-hydroxycyclohexyl)-propane and 1,1-bis-(hydroxymethyl)-cyclohex-3-ene, and from alcohols with aromatic nuclei, such as N,N-bis-(2-hydroxyethyl)-aniline and p,p'-bis-(2-hydroxyethylamino)-diphenylmethane. They can furthermore be obtained from mononuclear phenols, such as resorcinol and hydroquinone, and polynuclear phenols, such as bis-(4-hydroxyphenyl)methane (otherwise known as bisphenol F), 4,4'-dihydroxydiphenyl, 1,1,2,2-tetrakis-(4-hydroxyphenyl)-methane, 2,2-bis-(4-hydroxyphenyl)-propane (otherwise known as bisphenol A), and from novolaks formed by reaction of aldehydes, such as formaldehyde, acetaldehyde and benzaldehyde, with phenol itself and phenol which is ring-substituted by alkyl groups with in each case up to nine carbon atoms, such as 2-methylphenol and 4-tert.-butylphenol.

Poly-(N-glycidyl) compounds can also be used for the process according to the invention, for example N-glycidyl derivatives of amines, such as aniline, n-butylamine, bis-(4-aminophenyl)-methane and bis-(4-methylaminophenyl)-methane, triglycidyl isocyanurate and N,N'-diglycidyl derivatives of cyclic alkyleneureas, such as ethyleneurea and 1,3-propyleneurea, and of hydantoins, such as 5,5-dimethylhydantoin.

It is also possible to employ poly-(S-glycidyl) compounds, for example di-(S-glycidyl) derivatives of dithiols, such as ethane-1,2-dithiol and bis-(4-mercaptomethylphenyl) ether, but these are not preferred.

Glycidyl compounds in which the glycidyl groups are bonded to different hetero-atoms, for example p-(diglycidylamino-phenyl glycidyl ethers, are also suitable.

The glycidyl ethers, in particular those of mononuclear phenols, are preferably employed in the process according to the invention.

Suitable halogen-free inert organic solvents which contain in their molecule no group or grouping which is reactive towards the tin hydrides of the formula I or II and which can be employed in the process according to the invention are, for example, aliphatic hydrocarbons, such as pentane, hexane, heptane or octane, cycloaliphatic hydrocarbons, such as cyclohexane or cyclopentane, aromatic hydrocarbons, such as benzene, toluene or xylenes, and aliphatic or cyclic ethers, such as diethyl ether, dioxane or tetrahydrofuran.

The tin hydrides of the formula I and II to be employed in the process according to the invention are known compounds and can be prepared by the process described in "Journal of Applied Chemistry", July 1957, pages 366–368, or in "Synthesis", No. 10, October 1970, pages 499–509, for example by reducing the corresponding tin chlorides $R_3SnCl$ and $R_2SnCl_2$, in which each radical R is as defined for formula I or II, with LiAlH₄ to give the tin hydrides of the formula I or II.

Examples of suitable tin hydrides for the process according to the invention are triethyl-tin hydride, tri-n-propyl-tin hydride, tri-n-butyl-tin hydride, triphenyl-tin hydride, di-n-propyl-tin hydride, di-n-butyl-tin hydride and diphenyl-tin hydride.

The tin hydrides of the formula I, especially tri-butyl-tin hydride or triethyl-tin hydride, are preferably employed in the process according to the invention.

The amount of tin hydride of the formula I or II to be employed in the process according to the invention is chosen so that at least 1 H equivalent of tin hydride is present per equivalent of chlorine. An excess of tin hydride of the formula I or II is advantageously employed, and this can be of virtually unlimited size, but is preferably 1.2–20, in particular 1.5–13, equivalents of tin hydride per equivalent of chlorine.

Initiators which can be activated by heat or photochemically can be employed in the process according to the invention as initiators which form free radicals. Such agents which form free radicals are known. Some agents which form free radicals are substances which can be activated both photochemically (i.e. formation of free radicals triggered off by irradiation) and by means of heat. Examples of suitable initiators which can be activated photochemically are organic peroxides and hydroperoxides, α-halogen-substituted acetophenones, such as trichloromethyl 4'-tert.-butyl phenyl ketone, α-hydroxy-α-alkyl-substituted acetophenones, such as 2-hydroxy-2-methyl-1-phenylpropan-1-one, benzoin and alkyl ethers thereof (for example the n-butyl ether), α-methylbenzoin, benzophenones, such as benzophenone itself and 4,4'-bis-(dimethylamino)-benzophenone, O-alkoxycarbonyl derivatives of an oxime of benzil or 1-phenylpropane-1,2-dione, such as benzil (O-ethoxycarbonyl)-α-monoxime and 1-phenylpropane-1,2-dione 2-(O-ethoxycarbonyl)-oxime, benzil ketals, such as benzil dimethyl ketal, substituted thioxanthones, anthraquinones and photo-redox systems which consist of a mixture of a phenothiazine dye (for example methylene blue) or a quinoxaline (for example a metal salt of 2-(m- or p-methoxyphenyl)-quinoxaline-6'- or -7'-sulfonic acid) with an electron donor, such as benzenesulfinic acid or another sulfinic acid or a salt thereof, such as the sodium salt, or an arsine, a phosphine or thiourea.

Examples of suitable initiators which form free radicals and can be activated by heat, i.e. those which form free radicals at a considerable rate above room temperature, are organic or inorganic peroxides, for example peracids and salts and esters thereof, such as peracetic acid, perbenzoic acid, perphthalic acid, diisopropyl peroxydicarbonate, ammonium perborate or an alkali metal perborate and ammonium persulfate or an alkali metal persulfate, acyl peroxides, such as benzoyl peroxide, and, for example, cumyl peroxide, cumene hydroperoxide, hydrogen peroxide, cyclohexanone peroxide and ethyl methyl ketone peroxide, azo compounds, such as azo-bis-(isobutyronitrile), and sterically hindered phenyl-substituted alkanes, such as 2,3-dimethyl-diphenylbutane and 3,4-dimethyl-3,4-diphenylhexane. The preferred free radical initiators are those which can be activated by heat, such as azo-bis-(isobutyronitrile), cumene hydroperoxide and ketone peroxides, in particular azo-bis-(isobutyronitrile).

The initiators which form free radicals are usually employed in the process according to the invention in catalytic amounts, i.e. their content is in general between 0.1 and 5% by weight, based on the amount of glycidyl compound employed, preferably between 0.1 and 1.5% by weight.

The process according to the invention is preferably carried out at elevated temperatures, in particular in the temperature range from 60° to 110° C.

The reaction mixture can be worked up by customary separation methods. For example, it is possible either to remove the excess tin hydride of the formula I or II and the alkyl- or phenyl-tin chloride formed in the reaction by distillation under reduced pressure, after removal of the organic solvent, or, after removal of the organic solvent, to dissolve the glycidyl compound which remains in acetonitrile and to wash this solution with hexane or petroleum ether for the purpose of removing the organic tin compounds. The latter method is the preferred working up procedure.

The amounts of total chlorine and hydrolysable chlorine quoted in the following examples are determined potentiometrically as follows:

Total chlorine content: 25 ml of butylcarbitol (diethylene glycol monobutyl ether) are added to about 3 g of the glycidyl compound. The solution is heated under reflux for 20 minutes and then cooled to room temperature. After addition of 50 ml of acetic acid, the chlorine content is determined potentiometrically by means of 0.01 N silver nitrate solution.

Content of hydrolysable chlorine: About 5 g of the glycidyl compound are dissolved in 20 ml of toluene and 50 ml of a 0.1N potassium hydroxide solution are added. The solution is heated under reflux for 2 minutes and then cooled to 10 to 15° C. After addition of 50 ml of acetic acid, the chlorine content is determined potentiometrically by means of 0.01 N silver nitrate solution.

As already mentioned, the glycidyl compounds obtained by the process according to the invention are particularly suitable for applications in the electronics sector.

EXAMPLE 1

101 g of a bisphenol A diglycidyl ether which has been prepared industrially from bisphenol A and epichlorohydrin and has an epoxide content of 5.37 equivalents/kg, a total chlorine content of 0.16% by weight and a content of hydrolysable chlorine of 0.024% by weight are dissolved in 200 g of toluene. The solution is heated to 80° C. and 7.5 g of tri-n-butyl-tin hydride and 0.2 g of azobis-(isobutyronitrile) are added under an N₂ atmosphere. After the solution has been stirred at this temperature for 16 hours, the toluene is removed by distillation and the epoxy resin which remains is dissolved in 100 g of acetonitrile. The tributyltin chloride formed in the reaction and the excess tributyltin hydride is removed from this solution by washing it 10 times with 100 g of hexane each time. The bisphenol A diglycidyl ether obtained after the acetonitrile has been distilled off has an epoxide content of 5.36 equivalents/kg, a total chlorine content of 0.033% by weight and a content of 0.009% by weight of hydrolysable chlorine.

EXAMPLE 2

100 g of a cresol-novolak epoxy resin which has been prepared industrially from cresol-novolak and epichlorohydrin and has an epoxide content of 4.62 equivalents/kg, a total chlorine content of 0.13% by weight and a content of hydrolysable chlorine of 0.028% by weight are dissolved in 180 g of toluene. The solution is heated to 80° C. and 4.18 g of tri-n-butyl-tin hydride and 0.2 g of azo-bis-(isobutyronitrile) are added under an $N_2$ atmosphere. The reaction solution is kept at 80° C. and, after 1 hour, a further 0.1 g of azo-bis-(isobutyronitrile) is added to the reaction solution. This operation is repeated 3 times. After a total reaction time of 20 hours at 80° C., the reaction solution is worked up as in Example 1. A cresol-novolak epoxy resin with an epoxide content of 4.6 equivalents/kg, a total chlorine content of 0.032% by weight and a content of hydrolysable chlorine of 0.0084% by weight is obtained.

EXAMPLE 3

100 g of the cresol-novolak epoxy resin employed in Example 2 are dissolved in 200 g of toluene. The solution is heated to 80° C. and 4.5 g of triethyl-tin hydride and 0.1 g of azo-bis-(isobutyronitrile) are added under an $N_2$ atmosphere. The solution is kept at 80° C. and, after 1 hour, a further 0.1 g of azo-bis-(isobutyronitrile) is added. This operation is repeated 3 times. After a total reaction time of 22 hours at 80° C., the toluene is distilled off and the tin salt is removed from the epoxy resin by stripping with water. A cresol-novolak epoxy resin with an epoxide content of 4.56 equivalents/kg, a total chlorine content of 0.037% by weight and a content of hydrolysable chlorine of 0.02% by weight is obtained.

EXAMPLE 4

100 g of the bisphenol A diglycidyl ether employed in Example 1 are dissolved in 200 g of toluene. The solution is heated to 80° C. and 2.89 g of triethyl-tin hydride and 0.1 g of azo-bis-(isobutyronitrile) are added under a nitrogen atmosphere. The solution is kept at 80° C. and, after 1 hour, a further 0.1 g of azo-bis-(isobutyronitrile) is added. This operation is repeated 3 times. After a total reaction time of 22 hours at 80° C., the toluene is distilled off and the residual tin compounds are removed from the epoxy resin by vacuum distillation at 160° C./130 Pa. A bisphenol A diglycidyl ether with an epoxide content of 5.24 equivalents/kg, a total chlorine content of 0.0403% by weight and a content of hydrolysable chlorine of 0.033% by weight is obtained.

EXAMPLE 5

100 g of the cresol-novolak epoxy resin employed in Example 2 are dissolved in 100 g of toluene and under $N_2$ atmosphere 0.62 g of azo-bis-(isobutyronitrile) and 3.3 g of di-n-butyl-tin hydride are added. The solution is heated to 80° C. and kept at this temperature for four hours. Then the reaction solution is worked up as in Example 1. A cresol-novolak epoxy resin with an epoxy content of 4.6 equivalents/kg, a total chlorine content of 0.067% by weight and a content of hydrolysable chlorine of 0.0097% by weight is obtained.

EXAMPLE 6

100 g of the cresol-novolak epoxy resin employed in Example 2 are dissolved in 100 g of toluene and under $N_2$ atmosphere 0.62 g of azo-bis-(isobutyronitrile) and 5.79 g of triphenyl-tin hydride are added. The solution is heated to 80° C. and kept at this temperature for four hours. Then the reaction solution is worked up as in Example 1. A cresol-novolak epoxy resin with an epoxy content of 4.43 equivalents/kg, a total chlorine content of 0.0255% by weight and a content of hydrolysable chlorine of 0.0053% by weight is obtained.

What is claimed is:

1. A process for reducing the content of chlorine in a glycidyl compound in which the glycidyl groups are bonded to ether-oxygen, N or S atoms, which comprises reacting the glycidyl compound, dissolved in a halogen-free inert organic solvent, with a tin hydride of the formula I or II $$R_3SnH \qquad (I)$$

or $$R_2SnH_2 \qquad (II)$$

in which each radical R independently of one another is alkyl with 1 to 4 C atoms or phenyl, at least 1 equivalent of the tin hydride of the formula I or II being employed per equivalent of chlorine present, in the presence of a catalytic amount of an initiator which forms free radicals, and then isolating the glycidyl compound from the reaction solution.

2. The process according to claim 1, wherein a glycidyl ether is employed as the glycidyl compound.

3. The process according to claim 1, wherein a glycidyl ether of a polynuclear phenol is employed as the glycidyl compound.

4. The process according to claim 1, wherein a tin hydride of the formula I is employed as the tin hydride.

5. The process according to claim 1, wherein tri-n-butyltin hydride, triethyl-tin hydride or triphenyl-tin hydride is employed as the tin hydride of the formula I.

6. The process according to claim 1, wherein 1.2 to 20 equivalents of tin hydride of the formula I or II are employed per equivalent of chlorine.

7. The process according to claim 1, wherein 1.5 to 12 equivalents of tin hydride of the formula I or II are employed per equivalent of chlorine.

8. The process according to claim 1, wherein an initiator which forms free radicals and can be activated by heat is employed as the initiator.

9. The process according to either of claims 1 or 8, wherein azo-bis-(isobutyronitrile) is employed as the initiator.

10. The process according to claim 1, wherein the reaction is carried out in the temperature range from 60° to 110° C.

11. The process according to claim 1, wherein, after the reaction, the glycidyl compound is freed from the organic solvent and dissolved in acetonitrile and this solution is washed with hexane or petroleum ether.

* * * * *